United States Patent [19]

Tarasov et al.

[11] 3,996,146

[45] Dec. 7, 1976

[54] CLEAR SHAMPOO FORMULATION

[75] Inventors: Arthur Tarasov, Upper Montclair; Harvey S. Koenig, Randolph, both of N.J.

[73] Assignee: Warner-Lambert Company, Morris Plains, N.J.

[22] Filed: Aug. 1, 1975

[21] Appl. No.: 601,068

[52] U.S. Cl. .............................. 252/142; 252/542; 252/544; 252/545; 252/546; 252/547; 252/548; 252/DIG. 2; 252/DIG. 13; 424/70; 424/DIG. 2
[51] Int. Cl.$^2$ .................. C11D 10/02; C11D 3/37; C11D 1/90
[58] Field of Search .......... 252/544, 545, 546, 547, 252/548, 542, DIG. 2, DIG. 13, 142; 424/70, DIG. 2

[56] References Cited

UNITED STATES PATENTS

| | | | |
|---|---|---|---|
| 2,926,116 | 2/1960 | Keim | 260/78 SC X |
| 2,926,154 | 2/1960 | Keim | 260/78 SC X |
| 2,950,255 | 8/1960 | Goff | 252/DIG. 13 X |
| 3,313,734 | 4/1967 | Lang et al. | 252/546 X |
| 3,400,198 | 9/1968 | Lang | 252/544 X |
| 3,496,110 | 2/1970 | Shumway | 252/DIG. 13 X |
| 3,549,546 | 12/1970 | Moore | 252/DIG. 13 X |
| 3,816,616 | 6/1974 | Anguillo et al. | 424/70 |
| 3,912,808 | 10/1975 | Sokol | 424/70 |

FOREIGN PATENTS OR APPLICATIONS 2,344,522   3/1974   Germany

*Primary Examiner*—Harris A. Pitlick
*Attorney, Agent, or Firm*—Albert H. Graddis; Frank S. Chow; Anne M. Kelly

[57] ABSTRACT

An acid pH, clear shampoo formulation containing a solubilized cationic resin in a detergent system maintained within a pH range of approximately 4 to 6.7, is described. Dilution of the clear shampoo formulation during the hair washing operation causes precipitation of an anionic/cationic complex which plates out on the hair and provides more facile combing of freshly shampooed hair. Tangles, pulled-out hair and other discomforts normally encountered with hair shampooing are minimized. The acid pH, clear shampoo formulation of this invention is especially beneficial for damaged, bleached, or cold-waved hair. The deleterious effects of shampooing damaged hair with alkaline detergent systems are avoided by maintaining the clear shampoo formulation within the acid range.

14 Claims, No Drawings

CLEAR SHAMPOO FORMULATION

BACKGROUND OF THE INVENTION

1. Field of the Invention

The present invention relates to an improved hair shampoo system formulated to reduce tangles, pulled-out hair and general discomforts associated with the combing out of freshly shampooed hair.

2. Description of the Prior Art

Hair shampoo compositions containing various treatment agents for the hair are known. For example, in U.S. Pat. No. 2,756,178 a cream-type shampoo having incorporated therein a high percentage of lanolin is described. It is claimed that a residual amount of lanolin remains on the hair after washing and rinsing, distributed homogeneously throughout the hair. The lanolin serves as a hair dressing but does not impart a greasy appearance to the hair.

U.S. Pat. No. 3,580,853 and U.S. Pat. No. 3,761,417 describe anti-dandruff shampoos containing a water-soluble, cationic, nitrogen-containing polymer which is said to enhance the deposition and retention of the anti-dandruff agents on the hair surface.

U.S. Pat. No. 3,313,734 covers the use of quaternized methacrylate and other quaternized polymers in combination with anionic and nonionic sufactants in a shampoo which is said to improve the condition of the hair. In U.S. Pat. No. 3,400,198, a shampoo which is similarly formulated contains polyethyleneimine polymers in combination with anionic and amphoteric or polar nonionic detergents, has a pH of 7 to 10 and imparts wave set retention qualities to the hair.

U.S. Pat. No. 3,816,616 discloses a unitary shampoo and cream rinse composition wherein an aqueous solution of a cationic polymer, compatible with the anionic hair shampoo, imparts improved manageability, sheen and curl retention to the hair.

DESCRIPTION OF THE PARTICULAR EMBODIMENTS

A unique acid pH, clear shampoo formulation is described wherein certain cationic resins are solubilized in a multidetergent system maintained within approximately pH 4.0 to pH 6.7, preferably pH 5.0 to 6.0, most preferably pH 5.0. The cationic resin is solubilized within this pH range and a clear liquid product is obtained. However, upon dilution with water during the actual shampoo operation, precipitation of an anionic/cationic complex occurs and the complex has been found to adhere to the hair shaft following thorough rinsing of the hair.

The cationic resins suitable for use in the unique acid pH, clear shampoo formulation of this invention include quaternary homopolymers or copolymers derived from dimethyl diallyl ammonium salts; polyamide-epichlorhydrin resins; and copolymers of acrylamide with beta-methacryloyloxyethyltrimethyl ammonium methyl sulfate. In practice, from about 0.05% to about 2.5%, by weight, based on the weight of the total formulation, of the cationic resin is included in the multi-detergent system to provide the unique acid pH, clear shampoo of this invention. The quaternary polymers derived from dimethyl diallyl ammonium salts are water-soluble resins having an average molecular weight between 75,000 and 500,000, and may be characterized generally as high molecular weight homopolymers or copolymers having a molecular chain containing units of the formula:

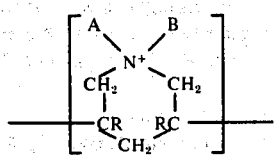

wherein R is hydrogen or methyl and A and B are methyl groups. A particularly suitable homopolymeric resin of this type having a molecular weight less than 100,000 is marketed commercially as a 40% aqueous solution under the tradename MERQUAT 100 by Merck & Co., Inc., Rahway, New Jersey. A particular quaternary copolymer formed from dimethyl diallyl ammonium chloride and an acrylamide is sold under the name MERQUAT 550 by Merck & Co., Inc., Rahway, New Jersey. MERQUAT 550 is an 8% aqueous solution of a copolymer having an average molecular weight of more than 500,000.

The polyamide-epichlorhydrin resins are water-soluble, thermosetting resins which may be prepared by reacting adipic acid with diethylene-triamine to form a basic polyamide of the formula:

which is further reacted with a mixture of an epichlorhydrin and dimethylamine such that the final resin obtained has a nitrogen content of 17.0–18.0% on a dry basis and a viscosity in 30% by weight aqueous solution of 350–800 centipoises at 20° C, as determined by a Brookfield viscometer using a No. 3 spindle at 30 rpm (or an equivalent method). Commercially available resins of the type are marketed under the tradenames CARTARETIN F4 and CARTARETIN F8 by Sandoz-Wander, Incorporated, Hanover, New Jersey.

The copolymers of acrylamide with beta-methacryloyloxyethyltrimethyl ammonium methyl sulfate are water-soluble and contain not more than 5-mole% of the beta-methacryloyloxyethyltrimethyl ammonium methyl sulfate. These resins may be further characterized as having moderate to high cationic functionality. Viscosities of 1% solutions of typical copolymers of this type as determined by a Brookfield viscometer are between 600–1200 centipoises. Representative cationic resins of this type are marketed commercially under the tradenames RETEN 205, 210, 220, SPX 1098, 1099, 1100, 1101, 1102, 1103, 1104, 1105 and 1106 and are available from Hercules, Incorporated, Cellulose and Protein Products Department, Wilmington, Delaware. RETEN 210 and RETEN 220 both have high cationic functionality; 1% solutions of RETEN 210 have a viscosity of 600–1000 centipoises and 1% solutions of RETEN 220 have a viscosity between 800–1200 centipoises.

Among the above cationic resin ingredients, the quaternary polymers derived from dimethyl diallyl ammonium salts (MERQUAT 100) and those described as polyamide-epichlorhydrin water soluble resins, particlarly CARTARETIN F4, are preferred.

The detergent system capable of solubilizing the above-described cationic resins within the stated acid pH range includes from about 10% to about 25%, by weight, preferably from about 12% to about 20%, by weight, based on the total weight of the shampoo formulation, of combinations of the following anionic detergents: the disodium salt of a half ester of alkanolamide sulfosuccinate; sodium lauryl ether sulfate; sodium N-methyl N-coconut oil acid taurate; the ammonium salt of alkylphenoxypoly(ethyleneoxy)ethanol sulfate; and the like.

The disodium salt of the half ester of alkanolamide sulfosuccinate may be further characterized as having an alkyl chain length of from $C_8$ to $C_{18}$. Such alkanolamide products are generally derived from coconut fatty acids or other natural or synthetic substitutes therefor.

The sodium N-methyl N-coconut oil acid taurate is prepared from a coconut oil acid characterized by a chain length distribution of from $C_8$–$C_{18}$ with at least 50% of the alkyl chains being $C_{12}$.

The ammonium salt of a sulfated alkylphenoxypoly (ethyleneoxy)ethanol has an alkyl chain length of from 8 to 12 carbon atoms, preferably 9 carbon atoms; and from about 2 to about 6 ethyleneoxy groups, averaging 4 such groups.

In order to solubilize the aforementioned cationic resin in the acid pH range, it has been found necessary to incorporate from about 4% to about 15%, by weight, preferably from about 5% to about 12%, by weight, based on the weight of the total formulation, of at least one of the following amphoteric detergents: an alkyldimethyl betaine; a substituted coco-imidazolinium betaine; a sulfated fatty polyoxyethylene quaternary nitrogen compound, or the like.

Suitable alkyldimethyl betaines are those in which the alkyl chain contains from 8 to 18, preferably with at least 46% of the chains containing 12 carbon atoms. Typical alkyldimethyl betaines include 2-(N-decyl-N,N-dimethylamino)-acetate, 2-(N-coco-N,N-dimethylamino)acetate, etc. The N-coco derivative, LONZAINE 12C, marketed commercially by the Lonza Company, Fairlawn, New Jersey is especially recommended.

The substituted coco-imidazolinium betaine compound suitable for use in the practice of this invention may be, for example, an amphoteric surfactant such as 1-hydroxymethyl-1-carboxymethyl-2-coco-imidazolinium betaine. An especially suitable complex fatty amide of this type is marketed commercially under the tradename ANTARON FC34 by GAF Corporation, New York, New York.

The sulfated fatty polyoxyethylene quaternary nitrogen compound which can be used in the shampoo formulation of this invention is prepared from aminated coco fatty acids and has a sulfated chain containing 10 to 20 moles of ethylene oxide. A typical sulfated fatty polyoxyethylene quaternary nitrogen compound of this type is sold commercially under the tradename ANTARON PC37 by Antara Chemicals, Division of General Aniline and Film Corp., New York, New York.

In order to maintain the acid pH in the clear shampoo formulation of this invention, it has been found that the addition of a weakly ionized acid such as acetic acid, citric acid, succinic acid, malic acid, and the like is necessary. Among these, acetic acid or citric acid is preferred since these acids are compatible with other ingredients in the formulation and suitable for use in shampoos and hair products. The acid may be added any time during formulation and mixing in an amount sufficient to bring the pH of the finished shampoo to approximately pH 4.0 to pH 6.7, preferably pH 5.0 to 6.0, most preferably pH 5.0.

The unique acid pH, clear shampoo formulation of this invention has been found to reduce tangles, pulled-out hair and other discomforts normally encountered in hair shampooing. The clear shampoo formulation is especially beneficial for use on bleached, damaged, or cold-waved hair where use of shampoos containing highly alkaline detergents has a very deleterious effect on the hair condition.

The need for reduction of tangles and pulled-out hair when hair is already in a damaged condition is, of course, obvious. However, special shampoo formulations now commercially available contain alkaline detergents which mitigate the beneficial effects of any treatment allegedly imparted by the conditioners in such shampoo formulations. The acid pH, clear shampoo formulation of this invention overcomes this difficulty. The cationic resin ingredient is effectively solubilized in the unique multi-detergent system at an acid pH to provide a clear shampoo formulation which precipitates a cationic/anionic complex upon dilution with water during shampooing.

The exact composition of the cationic/anionic complex and its method of attachment to the hair are not fully known. However, it is believed that the complex plates out during shampooing and physically attaches itself to certain sites on the hair shafts. Sufficient amounts of the complex remain on the hair shafts after thorough rinsing to reduce tangles and typical discomforts normally encountered in hair shampooing.

In spite of the fact that the exact nature of the "complex attachment" to the hair is unknown, beneficial results obtained can be scientifically demonstrated in the laboratory by the use of an Instron Tensiometer. A fixed comb is drawn at constant rate through a measured swatch of freshly shampooed virgin hair. The resultant stress-strain curve is integrated so that a numerical figure represents the area under the curve. Stress-strain curves for placebo shampooed hair show a marked repeatable difference (greater force required) when compared to curves for the same shampoo containing one of the solubilized cationic resins included in the formulation of this invention. Typical laboratory tests are more fully described below in Example 5.

Shampoo formulas of this invention may also contain ingredients commonly used in the art to improve viscosity, color, clarify, enhance foam, stabilize and preserve the shampoo. These ingredients, such as glycerine, propylene glycol, hexylene glycol, polyethylene glycol, methyl paraben, ethanol, etc., when used in amounts sufficient to achieve the result desired, do not affect the overall capability of the clear shampoo formulation of this invention.

In order to further illustrate the practice of this invention, the following examples are included:

EXAMPLE 1

A clear liquid shampoo formulation is prepared having the following composition:

|  | Parts by weight |
|---|---|
| Sodium lauryl ether sulfate (30% active) | 32.7 |
| Coco dimethyl betaine (36.5% active) | 13 |
| Ammonium salt of nonylphenoxypoly(ethyleneoxy)-ethanol sulfate (60% active) | 10 |
| Polyamide-Epichlorhydrin Resin (Cartaretin F4) | 1.5 |
| Fragrance | q.s. |
| Water | & q.s. to 100 |

The above ingredients are placed into a suitable container and thoroughly mixed. The pH is adjusted to between pH 5.0 and 6.0 with 5% acetic acid.

EXAMPLE 2

A clear liquid shampoo formulation is prepared having the following composition:

|  | Parts by weight |
|---|---|
| Disodium salt of half ester of coconut fatty amide sulfosuccinate (40% active) | 35 |
| Coco dimethyl betaine (36.5% active) | 16 |
| Ammonium salt of nonylphenoxypoly(ethyleneoxy)-ethanol sulfate (60% active) | 5 |
| Quaternary Polymer derived from dimethyl diallyl ammonium salts (MERQUAT 100) | 0.2 |
| Fragrance | q.s. |
| Water | & q.s. to 100 |

The above ingredients are placed into a suitable container and thoroughly mixed. The pH is adjusted to between pH 5.0 and 6.0 with 5% acetic acid.

EXAMPLE 3

A clear liquid shampoo formulation is prepared having the following compositions:

|  | Parts by weight |
|---|---|
| Sodium N-methyl-N "coconut oil acid" taurate (25% active) | 25 |
| Cocodimethyl betaine (36.5% active) | 16 |
| Ammonium salt of nonylphenoxypoly(ethyleneoxy)-ethanol sulfate (60% active) | 8 |
| MERQUAT 100 | 0.2 |
| Fragrance | q.s. |
| Water | & q.s. to 100 |

The above ingredients are placed into a suitable container and thoroughly mixed. The pH is adjusted to between pH 5.0 and 6.0 with 5% acetic acid.

EXAMPLE 4

A clear liquid shampoo formulation is prepared having the following composition:

|  | Parts by weight |
|---|---|
| Sulfated fatty polyoxyethylene quaternary nitrogen compound (ANTARON PC37) (75% active) | 8 |
| Complex fatty amide compound (ANTARON FC34) (38% active) | 15 |
| Sodium lauryl ether sulfate (30% active) | 13.5 |
| Ammonium salt of nonylphenoxypoly(ethyleneoxy)-ethanol sulfate (60% active) | 10 |
| Copolymer of acrylamide with beta-methacryloyloxyethyltrimethyl ammonium methyl sulfate (RETEN SPX 1098) | 0.5 |
| Fragrance | q.s. |
| Water | & q.s. to 100 |

The above ingredients are placed into a suitable container and thoroughly mixed. The pH is adjusted to between pH 5.0 and 6.0 with 5% acetic acid.

EXAMPLE 5

Shampoo Evaluation on Swatches of Hair

A. Two swatches of virgin hair are shampooed with a control shampoo consisting of 50 parts by weight of sodium lauryl ether sulfate and 50 parts by weight of water. After the shampoo hair is thoroughly rinsed, a fixed comb connected to an Instron Teniometer, is drawn at a constant rate through a measured portion of the swatch of hair 5 times, in rapid succession and the average force required to draw the comb through the hair is determined. The following measurements are obtained:

| Swatch No. 1 | Swatch No. 2 |
|---|---|
| 500 | 533 |
| 675 | 572 |
| 402 | 495 |
| 449 | 436 |
| 339 | 401 |
| avg. 473.0 | avg. 487.4 |

B. An acid shampoo is prepared as described in Example 1 (with the exception that the CARTARETIN F4 is omitted) to contain 32.7 parts by weight of sodium lauryl ether sulfate, 13 parts cocodimethyl betaine, 10 parts of the ammonium salt of nonylphenoxypoly(ethyleneoxy)ethanol sulfate, fragrance and water to 100 parts by weight; the pH is then adjusted to between 5.0 and 6.0 with 5% acetic acid. This shampoo is used to wash Swatch 1 from (A) above. After the shampooed hair is thoroughly rinsed, the fixed comb test is run 5 times. The same swatch is again shampooed, followed by the fixed comb test which is run 5 times. The following measurements are obtained for Swatch No. 1:

| First Shampoo | Second Shampoo |
|---|---|
| 640 | 598 |
| 460 | 522 |
| 450 | 465 |
| 430 | 487 |
| 467 | 445 |
| avg. 489.4 | avg. 503.4 |

C. The acid shampoo of Example 1 is used to shampoo Swatch No. 2 in (A) above and, after the shampooed hair is thoroughly rinsed, the fixed comb test is repeated 5 times. The same swatch is again shampooed and the fixed comb test is run 5 times. The following measurements are obtained for Swatch No. 2:

| First Shampoo | Second Shampoo |
|---|---|
| 445 | 493 |
| 440 | 408 |
| 371 | 420 |
| 356 | 361 |
| 370 | 319 |
| avg. 396.4 | avg. 400.2 |

D. A standard t test analysis is made between the control shampoo and each treatment shampoo for each hair swatch. The difference between the means of each group is divided by the means of the control group and multiplied by $10^2$ to derive the percent change in area under the curve. The following results are obtained:

|  | Swatch No. 1 - Resin-Free Shampoo | | |
|---|---|---|---|
|  | Control | First Shampoo | Second Shampoo |
| x | 473.00000 | 489.40000 | 503.40000 |
| SD | 127.57938 | 85.33346 | 60.10241 |
| SE | 57.05523 | 38.16228 | 26.87861 |

-continued

|  |  |  |
|---|---|---|
| $x_1-x_2$ |  | 16.40000 | 30.40000 |
| %change (increase) |  | 3.47 | 6.43 |

| Swatch No. 2 - Resin-Containing Shampoo | | | |
|---|---|---|---|
|  | Control | First Shampoo | Second Shampoo |
| x | 487.40000 | 396.40000 | 400.20000 |
| SD | 69.64409 | 42.53586 | 65.56447 |
| SE | 31.14578 | 19.02261 | 29.32132 |
| $x_1-x_2$ |  | 91.00000 | 87.20000 |
| %change (decrease) |  | 18.67 | 17.89 |

E. Results indicate that the swatch of hair shampooed with the acid shampoo formulation of Example 1 containing the solubilized cationic resin material required less force in the fixed comb test, since lower stress-strain curves are obtained for the resin-containing shampoo than for the resin-free shampoo. These results indicate that the swatch of hair shampooed with the Example 1 formulation of this invention had fewer tangles and was easier to comb through in the wet state.

EXAMPLE 6

Shampoo Evaluation on Human Subjects

Half head comparison tests of the shampoo of Example 2 on human subjects were conducted by shampooing one half of the hair with the shampoo of Example 2 and the other half of the hair with "Herbal Essence", a commercially available conditioning shampoo (Clairol, Inc., Stamford, Conn.) having pH of about 6.3. Results indicate that the side shampooed with the test shampoo had fewer tangles, had a slightly slippery feel and was easier to comb through in the wet state.

We claim:
1. An acid pH, clear shampoo formulation comprising:
   1. from about 0.05% to about 2.5% by weight, based on the weight of the total formulation, of a cationic resin selected from the group consisting of:
      A. quaternary polymers derived from dimethyl diallyl ammonium salts;
      B. polyamide-epichlorhydrin resins derived by reacting adipic acid with diethylene-triamine to form a basic polyamide resin which is further reacted with epichlorhydrin and dimethylamine; and
      C. copolymers of acrylamide with beta-methacryloyloxyethyltrimethyl ammonium sulfate containing not more than 5-mole% of beta-methacryloyloxyethyltrimethyl ammonium sulfate;
   2. from about 10% to about 25% by weight of at least two anionic detergents selected from the group consisting of:
      A. the disodium salt of a half ester of alkanolamide sulfosuccinate;
      B. sodium lauryl ether sulfate;
      C. sodium N-methyl N-coconut oil acid taurate; and
      D. the ammonium salt of a sulfated fatty alkyl-phenoxypoly (ethyleneoxy) ethanol sulfate;
   3. from about 4% to about 15% by weight of at least one amphoteric detergent selected from the group consisting of:
      A. an alkyldimethyl betaine;
      B. a substituted coco-imidazolinium betaine;
      C. a sulfated fatty polyoxyethylene quaternary nitrogen compound; and
   4. a sufficient amount of a non-toxic, non-irritating acid to maintain the pH of the shampoo formulation between from about 4.0 to about 6.7.

2. A shampoo formulation according to claim 1 wherein the anionic detergent combination is present in an amount of from about 12% to about 20% by weight; the amphoteric detergent is present in an amount of from about 5% to about 12% by weight; and wherein the acid is selected from the group consisting of acetic acid, citric acid, succinic acid and malic acid, and the pH is maintained within from about 5.0 to about 6.0.

3. A shampoo formulation according to claim 2 wherein the cationic resin is a water-soluble quaternary polymer derived from dimethyl diallyl ammonium salts, having an average molecular weight between 75,000 and 500,000, containing in its molecular chain repeating units of the formula:

$$\left[ \begin{array}{c} A \diagdown \diagup B \\ N^+ \\ CH_2 \diagup \diagdown CH_2 \\ | \quad \quad | \\ CR \diagdown \diagup RC \\ CH_2 \end{array} \right]$$

wherein R is hydrogen or methyl and A and B are each methyl.

4. A shampoo formulation according to claim 3 wherein the cationic resin is a copolymer of dimethyl diallyl ammonium chloride and acrylamide having an average molecular weight of 500,000.

5. A shampoo formulation according to claim 2 wherein the cationic resin is a water-soluble, polyamideepichlorhydrin resin prepared by reacting adipic acid with diethylenetriamine to form a basic polyamide of the formula:

$$CO.NH.CH_2.CH_2.NH.CH_2.CH_2.NH.CO.(CH_2)_4$$

which is further reacted with a mixture of epichlorhydrin and dimethylamine to obtain a polymer having a nitrogen content of about 17% to 18% by weight on a dry basis; said polymer having a viscosity in a 30% by weight aqueous solution of 350 to 800 centipoises at 20° C.

6. A shampoo formulation according to claim 2 wherein the disodium salt of a half ester of alkanolamide sulfosuccinate has an alkyl chain length of from 8 to 18 carbon atoms.

7. A shampoo formulation according to claim 2 wherein the sodium N-methyl N-coconut oil acid taurate has an alkyl chain length containing from 8 to 18 carbon atoms.

8. A shampoo formulation according to claim 2 wherein the ammonium salt of a sulfated alkylphenoxypoly(ethyleneoxy)ethanol has an alkyl chain length of from 8 to 12 carbon atoms; and contains from about 2 to about 6 ethyleneoxy groups.

9. A shampoo formulation according to claim 8 wherein, in the ammonium salt of the sulfated alkylphenoxy(ethyleneoxy)ethanol, the alkyl chain contains 9 carbon atoms and there is an average of 4 ethyleneoxy groups present.

10. A shampoo formulation according to claim 2 wherein the alkyldimethyl betaine has an alkyl chain of from 8 to 18 carbon atoms.

11. A shampoo formulation according to claim 2 wherein the alkyldimethyl betaine is selected from the group consisting of 2-(N-decyl-N,N-dimethylamino)acetate and 2-(N-coco-N,N-dimethylamino)acetate.

12. A shampoo formulation according to claim 2 wherein the amphoteric detergent is 1-hydroxymethyl-1-carboxymethyl-2-coco-imidazolinium betaine.

13. A shampoo formulation according to claim 2 wherein the sulfated fatty polyoxyethylene quaternary nitrogen amphoteric detergent has a sulfated chain containing 10 to 20 moles of ethyleneoxide.

14. A shampoo formulation according to claim 2 wherein the acid ingredient is selected from the group consisting of acetic acid and citric acid; and wherein the pH of the shampoo formulation is maintained at about 5.0.

* * * * *